United States Patent [19]
Chao

[11] Patent Number: 5,651,146
[45] Date of Patent: Jul. 29, 1997

[54] SPORTS GOGGLES HAVING SHOCK ABSORBING MECHANISM

[76] Inventor: David Yinkai Chao, 1120 Green Acre Rd., Towson, Md. 21204

[21] Appl. No.: 642,851

[22] Filed: May 6, 1996

[51] Int. Cl.$^6$ ............................................. A61F 9/02
[52] U.S. Cl. ................................. 2/431; 2/446; 2/452
[58] Field of Search .......................... 2/431, 439, 445, 2/446, 452, 448, 449

[56] References Cited

U.S. PATENT DOCUMENTS

| | | | |
|---|---|---|---|
| 3,051,961 | 9/1962 | Clark | 2/9 X |
| 4,852,185 | 8/1989 | Olson | 2/9 |
| 5,495,623 | 3/1996 | Leonardi | 2/431 |

Primary Examiner—Peter Nerbun
Attorney, Agent, or Firm—Charles E. Baxley, Esq.

[57] ABSTRACT

A pair of sports goggles include a frame for securing lenses and including two legs extended from the side portions thereof. A resilient belt includes two end portions secured to the legs for securing the frame to a head of a user. A soft outer covering is engaged on the legs and/or the bridge member or on all of the frame for contacting with the head of the user. The soft outer covering includes a chamber arranged inwardly of the legs, bridge and/or frame relative to the head of the user, so as to form a shock absorption mechanism for the sports goggles and to provide comfort as the belt is tightened.

3 Claims, 2 Drawing Sheets

SPORTS GOGGLES HAVING SHOCK ABSORBING MECHANISM

BACKGROUND OF THE INVENTION

1. Field of the Invention

The present invention relates to a goggle frame, and more particularly to a pair of sports goggles having a shock absorbing mechanism.

2. Description of the Prior Art

Typical sports goggles comprise a frame body for securing lenses therein and a resilient belt secured to the end portions of the frame body for securing the frame body to the head of the user. However, the frame body normally is made as a rigid body such that the user may feel uncomfortable when the resilient belt is tightly tightened onto the head of the user. The frame body may include a soft outer covering thereon. However, the soft outer covering may not be provided for effectively absorbing shocks and vibrations that may be transmitted to the head of the user.

The present invention has arisen to mitigate and/or obviate the afore-described disadvantages of the conventional sports goggles.

SUMMARY OF THE INVENTION

The primary objective of the present invention is to provide a pair of sports goggles which includes a soft outer covering engaged around the frame body and which includes a chamber formed in the covering so as to form an excellent shock absorption configuration, such that the user may feel more comfortable.

In accordance with one aspect of the invention, there is provided a pair of sports goggles comprising a frame body for securing lenses therein, the frame body including two side portions each having a leg extended therefrom and including a middle portion having a bridge member provided therein, a resilient belt including two end portions secured to the legs for securing the frame body to a head of a user, and a soft outer covering engaged on the legs and/or engaged on the bridge member and/or engaged on all of the frame body for contacting with the head of the user, the soft outer covering including a chamber formed therein and arranged closer to the head of the user than its respective leg, bridge and/or frame body, so as to form a shock absorption configuration in the soft outer covering of the sports goggles, whereby the sports goggles fit a user more comfortably when the resilient belt is tightened and the head of the user is cushioned from impacts on the sports goggles.

Further objectives and advantages of the present invention will become apparent from a careful reading of a detailed description provided hereinbelow, with appropriate reference to accompanying drawings.

DETAILED DESCRIPTION OF THE PREFERRED EMBODIMENT

Figure 1:
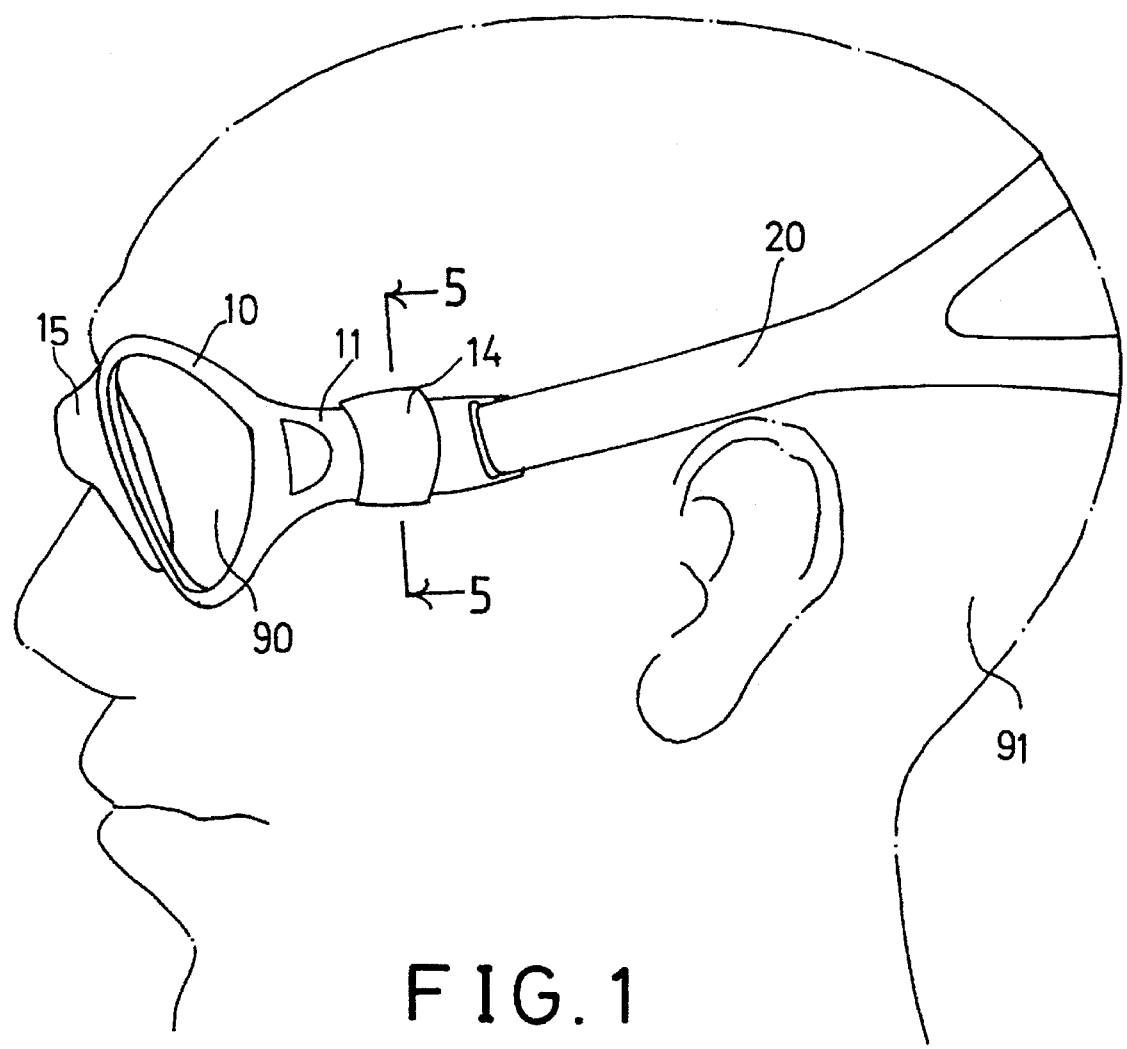
FIG. 1 is a side view of a pair of sports goggles in accordance with the present invention, illustrating operation of the sports goggles.
Figure 2:
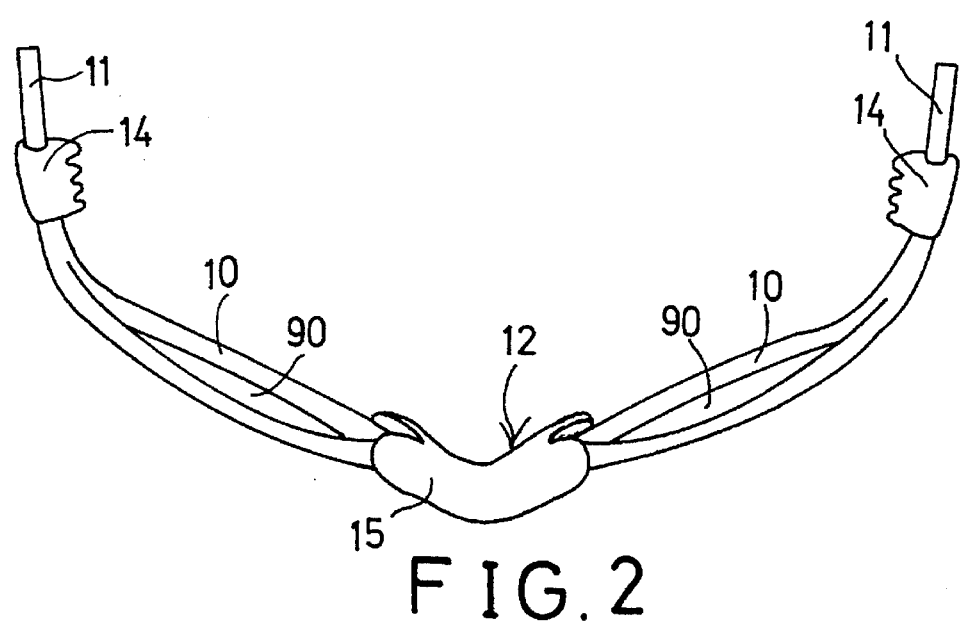
FIG. 2 is a top view of the sports goggles.
Figure 3:
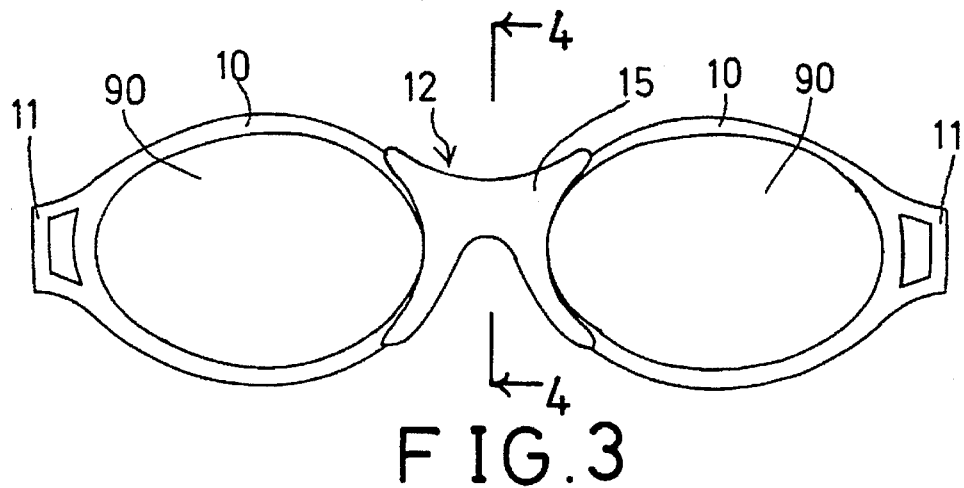
FIG. 3 is a front view of the sports goggles.

Referring to the drawings, and initially to FIGS. 1 to 5, a pair of sports goggles in accordance with the present invention comprises a frame body 10 for securing lens 90 therein. The frame body 10 includes two side portions each having a leg 11 extended therefrom for engaging with the end portions of a resilient belt 20 which may be provided for securing the frame body 10 to the head 91 of a user. It is to be noted that the bridge member 12 and the legs 11 are the portions where the user likely is made most uncomfortable from the tightening force of the resilient belt when the resilient belt is tightly tightened onto the head of the user.

Figure 4:
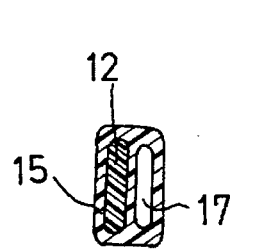
FIGS. 4 and 5 are cross sectional views of the sports goggles, taken along lines 4—4 and 5—5 of FIG. 3 and of FIG. 1 respectively.
Figure 5:
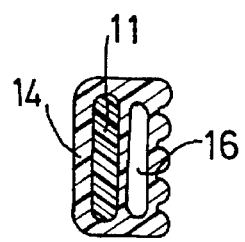

The frame body 10 further includes three soft outer coverings 14, 15 provided and engaged on the legs 11 and the bridge member 12. The soft outer coverings 14, 15 preferably are made of soft and resilient materials, such as silicon material, rubber material, foamable material, e.g. polyurethane. The soft outer coverings 14, 15 is soft such that the user feels more comfortable. The soft outer coverings 14, 15 each further includes a chamber 16, 17 formed therein for containing air or liquid therein so as to form an excellent shock absorption configuration. The chambers 16, 17 are each formed in a position closer to the head of the user than its respective bridge member 12 and leg 11 (FIGS. 4 and 5). Typically, the bridge member 12 is the place where the nose of the user should suffer the greatest from tightening force applied to the resilient belt 20. The chamber 17 formed in the bridge member 12 may absorb most of the force applied onto the head of the user such that the user feels more comfortable.

Figure 7:
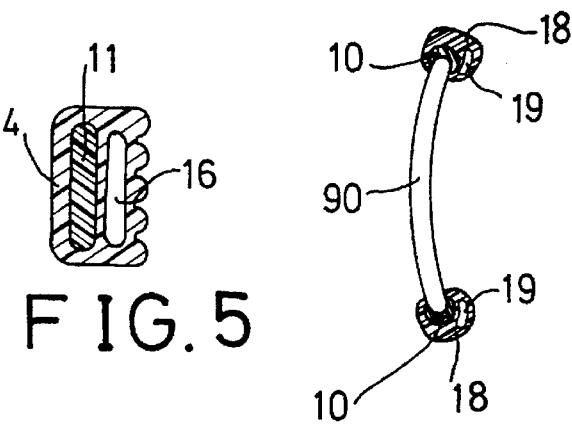
FIG. 7 is a cross sectional view taken along lines 7—7 of FIG. 6.
Figure 6:
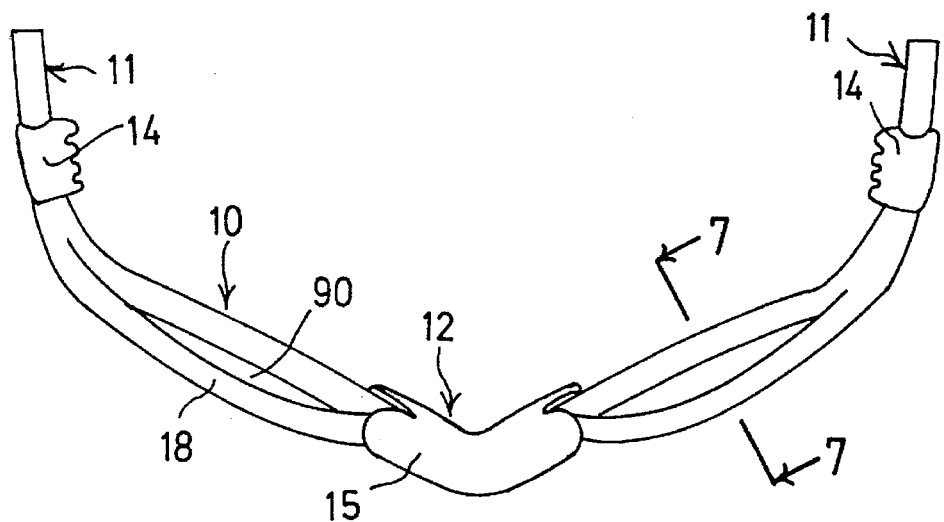
FIG. 6 is a top view illustrating another application of the sports goggles.

It is to be noted that, as shown in FIGS. 6 and 7, in addition to the bridge member 12 and the legs 11, the whole sports goggles may include a soft outer covering 18 engaged thereon and may include chamber 19 formed within the soft outer covering 18 for receiving air or liquid or water therein, so as to form an excellent shock absorption configuration.

Accordingly, the sports goggles in accordance with the present invention includes a soft outer covering engaged around the frame body and includes a chamber formed in the soft outer covering in proximity with the user's head so as to form an excellent shock absorption configuration, such that the user feels more comfortable and is protected against impacts on the sports goggles.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. A pair of sports goggles, comprising:
   a frame body for securing lenses therein, said frame body including two side portions each having a leg extended therefrom,
   a belt including two end portions secured resiliently to said legs for securing said frame body to a head of a user, and
   a soft outer covering engaged on said legs for contact with the head of the user, said soft outer covering including a pair of chambers each formed therein, each of said chambers being positioned inwardly of one of said legs relative to the head of the user so as to form a shock absorption configuration for said sports goggles and to provide comfort as the belt is tightened.

2. A pair of sports goggles, comprising:

a frame body for securing lenses therein, said frame body including two side portions each having a leg extended therefrom and including a middle portion having a bridge member provided therein, a belt including two end portions secured resiliently to said legs for securing said frame body to a head of a user, and a soft outer covering engaged on said bridge member for contact with the head of the user, said soft outer covering including a chamber formed therein, said chamber being positioned inwardly of the bridge member relative the head of the user, so as to form a shock absorption configuration for said sports goggles and to provide comfort as the belt is tightened.

3. A pair of sports goggles, comprising:

a frame body for securing lenses therein, said frame body including two side portions each having a leg extended therefrom and including a middle portion having a bridge member provided therein, a belt including two end portions secured resiliently to said legs for securing said frame body to a head of a user, and a soft outer covering engaged on said frame body for contact with the head of the user, said soft outer covering including a chamber formed therein, said chamber being positioned inwardly of said frame body relative the head of the user, so as to form a shock absorption configuration for said sports goggles and to provide comfort as the belt is tightened.

* * * * *